United States Patent
Sugi et al.

(10) Patent No.: US 7,119,042 B2
(45) Date of Patent: Oct. 10, 2006

(54) CATALYST COMPOSITION FOR THE ISOMERIZATION OF N-PARAFFIN AND A PROCESS FOR ISOMERIZING N-PARAFFIN

(75) Inventors: Yoshihiro Sugi, Gifu (JP); Yoshihiro Kubota, Kokubunji (JP); Yoichi Nishimura, Yokohama (JP); Puspa Ratu, Gifu (JP)

(73) Assignee: Gifu University, Gifu (JP)

( * ) Notice: Subject to any disclaimer, the term of this patent is extended or adjusted under 35 U.S.C. 154(b) by 207 days.

(21) Appl. No.: 10/800,395

(22) Filed: Mar. 10, 2004

(65) Prior Publication Data
US 2005/0277800 A1 Dec. 15, 2005

(30) Foreign Application Priority Data
Mar. 10, 2003 (JP) ............................. 2003-064024

(51) Int. Cl.
*B01J 29/06* (2006.01)
*C07C 5/22* (2006.01)

(52) U.S. Cl. .................. 502/65; 502/73; 423/716; 423/DIG. 27; 585/739

(58) Field of Classification Search ............... 423/716, 423/DIG. 27; 502/65, 73; 585/739; 208/135
See application file for complete search history.

(56) References Cited

U.S. PATENT DOCUMENTS

| | | | |
|---|---|---|---|
| 3,308,069 A | | 3/1967 | Wadlinger et al. |
| RE28,341 E | | 2/1975 | Wadlinger et al. |
| 4,837,396 A | * | 6/1989 | Herbst et al. .................. 502/67 |
| 4,855,036 A | * | 8/1989 | Chiang et al. .......... 208/120.15 |
| 5,095,169 A | * | 3/1992 | Skeels et al. ................ 585/739 |
| 5,716,896 A | * | 2/1998 | Knifton et al. .............. 502/113 |
| 6,933,418 B1 | * | 8/2005 | Kelly et al. .................. 585/467 |

FOREIGN PATENT DOCUMENTS

| | | | |
|---|---|---|---|
| EP | 1138662 A1 | | 10/2001 |
| JP | 5-201722 | | 8/1993 |
| JP | 6-91174 | | 4/1994 |
| JP | 2003-190802 | * | 7/2003 |
| WO | WO94/13584 | | 6/1994 |

OTHER PUBLICATIONS

P.R. Hari Prasad Rao, et al., "Crysallization of high silica BEA by dry gel conversion", Applied Catalyst A: General 166(1998) 97-103.

* cited by examiner

Primary Examiner—David Sample
(74) Attorney, Agent, or Firm—Cooper & Dunham LLP

(57) ABSTRACT

Provided is a catalyst composition for the isomerization of n-paraffin which comprises a β-zeolite having been synthesized according to a dry gel process and contains cerium, the β-zeolite being characterized in that it has an average particle diameter of 0.01~0.1 μm and the proportion of the cerium in the β-zeolite is within the range of 0.001~0.2 in terms of the atomic ratio of the silicon atom in the β-zeolite to the cerium atom, i.e. [Ce]/[Si] as well as a process for isomerizing n-paraffin which comprises bringing n-paraffin into contact with the catalyst composition as set forth above.

4 Claims, 1 Drawing Sheet

F I G. 1
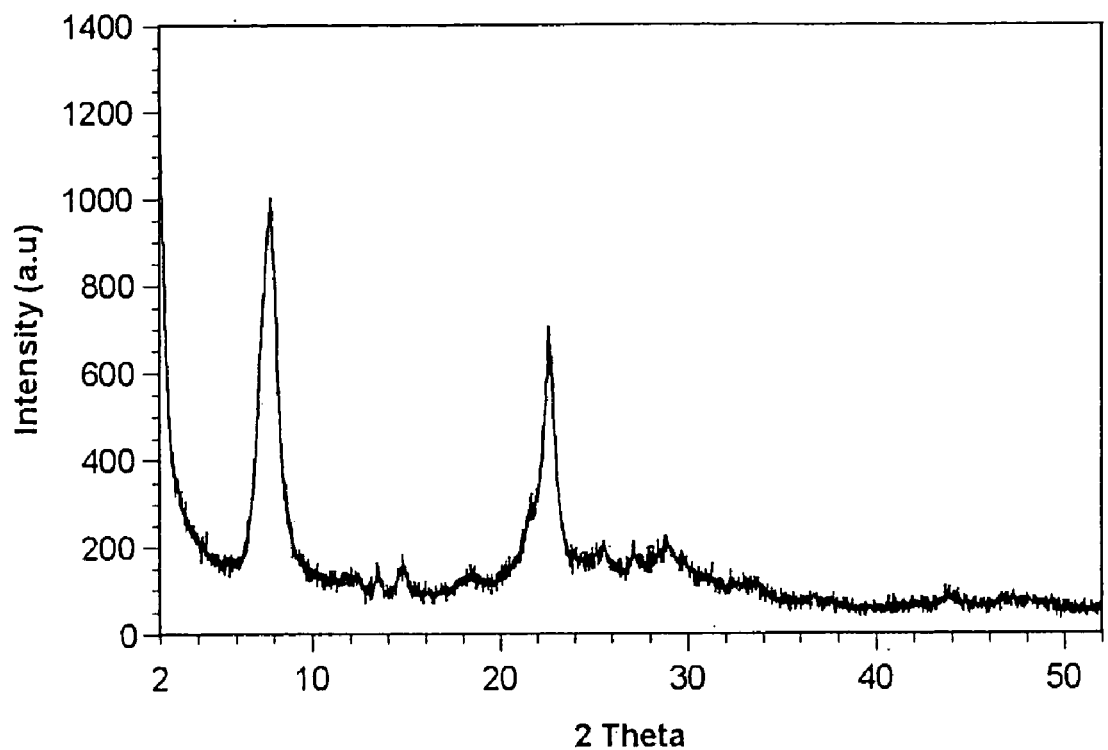
F I G. 2
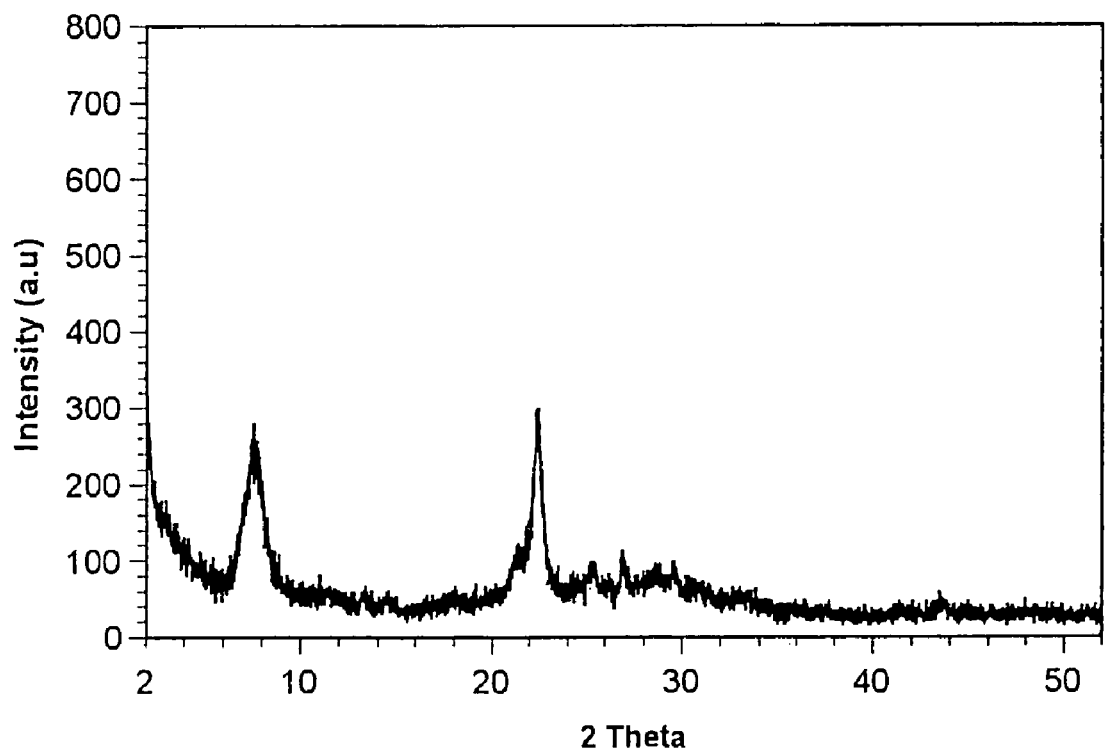

CATALYST COMPOSITION FOR THE ISOMERIZATION OF N-PARAFFIN AND A PROCESS FOR ISOMERIZING N-PARAFFIN

BACKGROUND OF THE INVENTION

1. Field of the Invention

The present invention relates to a catalyst composition for the isomerization of n-paraffin and a process for isomerizing n-paraffin. More particularly, the present invention relates to a catalyst composition for the isomerization of n-paraffin, which comprises a specific β-zeolite as well as a process for isomerizing n-paraffin in the presence of the catalyst composition.

2. Description of the Prior Art

It is known heretofore that n-paraffin existing in a gasoline fraction is of a low octane value and is not preferable as a fuel oil for automobiles employing gasoline. On the other hand, isoparaffin, an isomer of the n-paraffin, is higher in the octane value so that it is required to increase the content of isoparaffin in gasoline. Consequently, isomerization of n-paraffin is known to be an important process for the production of gasoline. Known as an industrial scale isomerization process is a process wherein a chlorine-treated alumina carrying platinum thereon (Pt—$Al_2O_3$) is used. According to this process, however, chlorine is liberated from the catalyst and, as a result, a source of chlorine has to be supplemented at all times. Further, the liberated chlorine induces corrosion of apparatus and any trace chlorine retained in the produced oil causes a problem of environmental pollution due to chlorine. In order that a catalyst life is prolonged, it is necessary to purify the crude oil paraffin containing water, sulfur value and the like causing inactivation to have a concentration of 1 ppm or lower. For these reasons, there is a great demand of developing a clean isomerization process. Crystalline aluminosilicates (zeolite), zirconia sulfate, molybdenum trioxide, etc. are known heretofore as a catalyst for the isomerization of n-paraffin lower in environmental load. Among the crystalline aluminosilicates, β-zeolite is known to exhibit a high degree of isomerization activity.

β-Zeolite is an aluminosilicate comprised of three-dimensional 12-oxygen membered-ring micropores, and its crystalline structure and chemical composition are disclosed in Atlas of Zeolite Framework Type s, 5$^{th}$ Revised Edition 2001, Ch, Baerlocher, W. M. Meier, D. H. Olson, 2001, Elsevier. As to the process for preparing β-zeolite, it is disclosed in various literatures, for example, U.S. Pat. No. 3,308,069; U.S. Pat. No. 4,642,226; Japanese Laid-open Patent Appln. No. Hei. 5-201722; Japanese Laid-open Patent Appln. No. Hei. 6-91174; Japanese Published Patent Appln. No. 8-509452; etc. In addition, a synthetic method of β-zeolite according to the so-called dry gel process is disclosed in Topics in Catalysis, 9, 1441 (1999).

β-Zeolite is excellent in isomerizing ability of n-paraffin but has such a drawback that a rapid deterioration in the activity takes place within a short period of time on account of precipitation of a large amount of carbon, thus shortening the catalyst life. The use of a zeolite carrying a noble metal thereon is adopted as a means for inhibiting reduction of the catalytic activity. For suppressing the reduction of the catalytic activity completely, however, it is necessary to inhibit the inherent ability of the catalyst for precipitation of carbon. Hence, there is a great demand for developing a novel catalyst capable of decreasing the precipitation of carbon on isomerization of n-paraffin.

SUMMARY OF THE INVENTION

1. The Subject to be Solved by the Invention:

It is therefore an object of the present invention to provide a novel catalyst composition comprised of a specific β-zeolite for the isomerization of n-paraffin capable of decreasing the precipitation of carbon on isomerization.

It is another object of the present invention to provide a process for the preparation of the novel catalyst composition comprised of the β-zeolite for the isomerization of n-paraffin wherein the β-zeolite is synthesized by a dry gel process.

It is still another object of the present invention, to provide a process for isomerizing n-paraffin wherein the aforesaid catalyst is employed for the isomerization.

Other and further objects, features and advantages of the present invention will be apparent more fully from the following description.

2. The Means for Solving the Subject:

In accordance with one embodiment of the present invention, there is provided a catalyst composition for the isomerization of n-paraffin which comprises a β-zeolite having been synthesized according to a dry gel process and contains cerium, the β-zeolite being characterized in that it has an average particle diameter of 0.01~0.1 μm and the proportion of the cerium in the β-zeolite is within the range of 0.001~0.2 in terms of the atomic ratio of the silicon atom in the β-zeolite to the cerium atom, i.e. [Ce]/[Si].

In accordance with another embodiment of the present invention, there is provided a process for isomerizing n-paraffin which comprises bringing n-paraffin into contact with the catalyst composition as set forth above.

BRIEF DESCRIPTION OF THE DRAWINGS

FIG. 1 is an X-ray diffraction pattern showing in detail the structure of the zeolite obtained in Example 1.

FIG. 2 is an X-ray diffraction pattern showing in detail the structure of the zeolite obtained in Comparative Example 3.

DETAILED DESCRIPTION OF THE INVENTION

The n-paraffin used in the present invention as a starting material is a linear saturated hydrocarbon of normally liquid paraffin series having 4~16, preferably 6~12 carbon atoms and generally includes light mineral oils and, in particular, a gasoline fraction, Illustrative of the n-paraffin are, for example, n-butane, n-pentane, n-hexane, n-heptane, n-octane, n-nonane, n-decane, n-dodecane, tetradecane, etc. usually in the form of a mixture of homologs. Such paraffin alone or a mixture of n-paraffin with other hydrocarbon or hydrocarbons, for example, isoparaffin can be used as a raw material for the reaction of the present invention. The octane value of the final product depends on the form of the resultant isoparaffin and on the quantity thereof. The proportion of n-paraffin to isoparaffin depends on equilibrium of these components at the reaction temperature so that the isomerization rate will become higher and the octane value of the product becomes higher as a mixing ratio of other hydrocarbons in the starting material becomes lower. Accordingly, n-paraffin alone is preferable as the starting material.

In the present invention, the catalyst composition for the isomerization of n-paraffin is composed of a β-zeolite which contains cerium element and has been synthesized according to the so-called dry gel process. This β-zeolite is referred to hereinafter briefly as Ce-βZ. The content of cerium in Ce-βZ is 0.001~0.2, preferably 0.002~0.1 in terms of the atomic ratio of cerium atom [Ce] to silicon atom [Si], i.e. [Ce]/[Si].

On synthesis of the aforesaid Ce-βZ according to the dry gel process, (i) an alkali metal cationic source, (ii) $Al_2O_3$ source, (iii) $SiO_2$ source, (iv) an organic template, and (v) water together with (vi) cerium source are used.

Sodium hydroxide or potassium hydroxide is used as the alkali metal cationic source (i).

An aluminum compound such as aluminum sulfate, sodium aluminate, aluminum isopropoxide, alumina or the like is used as the $Al_2O_3$ source (ii).

A silicon compound such as colloidal silica, silica hydrogel, silicic acid, a silicate, silica gel, ethyl orthosilicate, methyl orthosilicate or the like is used as the $SiO_2$ source (iii).

Any of the compounds capable of affording the β-zeolite can be used as the organic template (iv) and various organic compounds heretofore known containing nitrogen or phosphorus can be used. Examples of these compounds include primary, secondary and tertiary amines as well as quaternary ammonium compounds. Illustrative of the amine compounds are, for example, trimethylamine, triethylamine, tripropylamine, ethylenediamine, propylamine, diethylamine, benzylamine, pyridine, and piperizine. Illustrative of the ammonium compounds are, for example, hydroxides or various salts (chloride or bromide) of tetramethylammonium, tetraethylammonium tetrapropylammonium and dibenzyldimethylammonium.

Cerium salts such as cerium nitrate, cerium acetate, etc.; and cerium alkoxides such as cerium ethoxide, cerium methoxide, etc. is used as the cerium source (v).

A molar ratio of the chemical composition of Ce-βZ used in the present invention is:

$SiO_2/Al_2O_3$: 20~300, preferably 60~200
$CeO_2/SiO_2$: 0.001~0.2, preferably 0.002~0.1
$OH/SiO_2$: 0.2~0.6, preferably 0.4~0.5
$H_2O/SiO_2$: 5~30, preferably 10~20
$M/SiO_2$: 0.04~0.10, preferably 0.06~0.08
$R/SiO_2$: 0.2~0.6, preferably 0.3~0.5 wherein M stands for an alkali metal cation and R for an organic template.

As a process for preparing β-zeolite containing cerium, there is known a hydrothermal method wherein the Ce-containing β-zeolite is prepared by impregnating a preliminarily prepared β-zeolite with a solution of a cerium salt or a cerium alkoxide such as cerium ethoxide or methoxide, thereby carrying a cerium salt or alkoxide thereon. Alternatively, such cerium-containing β-zeolite can be prepared by subjecting a β-zeolite preliminarily synthesized by using a cerium salt to an ion-exchange treatment where the proton of the β-zeolite is exchanged with cerium cation.

However, the present inventors' research has made aware that the β-zeolite obtained according to the above methods is not yet satisfactory as isomerization catalyst for n-paraffin.

As a result of the inventors' extensive research made for improving the above methods by altering the method for synthesizing β-zeolite and checking the isomerization effect of n-paraffin, it has now been found surprisingly that Ce-βZ synthesized according to the dry gel process exhibits a high degree of isomerization effect for n-paraffin, less precipitation of carbon, and a prolonged catalyst life. The present invention has been accomplished in the basis of the above finding.

In order to synthesize Ce-βZ according to the dry gel process, an $Al_2O_3$ source, a $SiO_2$ source, a cerium source, an alkali metal cationic source, an organic template, and water are mixed to form a reaction mixture which is heated at 80~90° C. with stirring and then dried to obtain a solid matter (dry gel). This solid matter is pulverized to form a powdery substance. An average particle diameter of the powdery substance is 0.1~100 μm, preferably 10~50 μm.

The powdery substance is then maintained at 100~200° C., preferably 150~180° C. in the presence of steam vapor whereby the substance is crystallized.

This crystallized product is baked at a temperature of 450~700° C., preferably at 500~600° C. for combustion of the organic template and reacted with a solution of ammonium nitrate to form an ammonium product. This product is baked thereafter at 450~700° C., preferably at 500~600° C. to obtain Ce-βZ of H type. A particle diameter of this Ce-βZ is 0.01~0.1 μm.

The fine particulate Ce-βZ product thus obtained may be used as such for an isomerization catalyst but usually is subjected to pressure molding whereby the product is used in the form of a shaped article. The form of the article in this case may be any of the proper shape such as granular, spherical, cylindrical, hollow-cylindrical, pellet or the like shape.

On molding of the catalyst, an inert inorganic skeleton agent in various shapes may be used with a view to increasing the surface area of the catalyst. Utilizable as the skeleton agent are silica, bentonite, limestone and other known inert skeleton agent in various shapes.

It is also possible to use a molding binder as an assistant in the production of molded articles from particulate Ce-βZ. Such molding binder includes α-alumina or the like substance which is inert to the catalytic reaction and has a small surface area.

In order to carry out the isomerization of n-paraffin in the present invention, the n-paraffin is merely brought into contact with a catalyst comprising Ce-βZ. In this case, hydrogen is preferably used as reaction atmosphere for inhibit the precipitation of carbon. In the present invention, the precipitation of carbon is inherently suppressed so that the life of the catalyst is prolonged to operate the isomerization stably.

The reaction temperature (contact temperature) is within the range of 300~500° C., preferably 350~450° C. The reaction pressure is within the range of 0.5~100 atm. pressure, preferably 1~10 atm. pressure. A variety of modes such as a fixed bed, a fluidized bed, and a moving bed can be adopted as a method of contact.

EXAMPLES

The present invention will now be illustrated in more detail by way of Examples and Comparative Examples.

Example 1

(Preparation of Ce-βZ According to the Dry Gel Process)

A 35 wt. % aqueous solution containing 0.5 mmol of tetraethylammonium hydroxide (TEAOH) was mixed with a 25.2 wt. % of aqueous solution of 0.5 mmol of NaOH. To this mixture was added 7.51 g of a colloidal silica (Ludox HS-40) containing 50 mmol of $SiO_2$ and the whole was stirred for 30 minutes.

A solution of 0.01 mmol of $Al_2(SO_4)_3$ in 5.40 ml of warmed distilled water was then added to this mixture, and the whole was agitated for 30 minutes. To the mixture was added 00133 mmol of $Ce(NO_3)_3$ and the whole was then sired for 2 hours.

A gel thus obtained was dried with stirring on an oil bath kept at 80~90° C. for 2.5 hours. At the time of the gel becoming highly viscous, a Teflon® rods were added to the viscous matter and stirred until dryness (for about 30 minutes).

A white solid matter thus obtained was pulverized to a fine particulate powder and moved to a cup (inner diameter: 37 mm, height: 55 mm) made of Teflon®. This cup was allowed to enter in an autoclave (125 ml) the inside of which was lined with Teflon® whereupon a small amount of water (about 0.2 g per g of the dry gel) was allowed to be coexistent. By heating this autoclave for 2 days at 175° C., the dry gel was crystallized. The autoclave was then cooled with cold water and the resultant zeolite was taken out from the cup, washed with water and dried at room temperature.

The zeolite was then baked at 550° C. to burn the organic template (TEAOH) contained therein. An aqueous solution of ammonium nitrate was acted on the based product to convert it into the ammonium salt, and then baked for 7 hours at 550° C. whereby a β-zeolite containing Ce (Sample 1) of proton type (Model H) was obtained.

A chemical composition (molar ratio) of this zeolite was as shown below:

$SiO_2$: 1, $Al_2O_3$: 001, $CeO_2$: 0.0062

An X-ray diffraction pattern of this zeolite is shown in detail in FIG. 1.

In addition, the structure of this zeolite was confirmed by various analytical methods of ICP, TG-DTA, IR, $NH_3$-TPD, and NMR.

Example 2

(Isomerization of n-hexane)

Using the β-zeolite (Ce-βZ of type H, Sample 1) containing cerium obtained in Example 1 as catalyst, isomerization of n-hexane was carried out in the following manner:

At a flow rate of 0.15 ml/minute, n-hexane was allowed to pass together with a carrier gas ($N_2$) at a flow rate of 20 ml/minute through a flowing-type reactor filled with 1 g of the catalyst. In this case, the reaction temperature was maintained at 400° C. and the reaction pressure was kept under 1 atm. pressure.

A selection rate of the resultant isoparaffin was defined by the following formula:

Selection rate of isoparaffins=$(X/Y) \times 100$ wherein X stands for amounts of the six hydrocarbons 2-MP+3-MP+2,3-DMB+2,2-DMB+2-MB+1B formed, and Y stands for an amount of n-hexane reacted. In the above formulas, 2-MP is methylpentane, 3-MP is 3-methylpentane, 2,3-DMB is 2,3-dimethylbutane, 2,2-DMB is 2,2-dimethylbutane, 2-MB is 2-methylbutane, and 1-B is isobutene.

Accordingly, the yield of isoparaffin is defined by the following formula:

Yield of isoparaffin=(selection rate of isoparaffin × Y)×100

Table 1 shows the flow time (passing time) in case of using Sample 1, a conversion rate of n-hexane, a yield and selection rate of isoparaffin, and an amount of coke precipitated (% by weight). At the initial stage of the reaction, deterioration of the activity was found due to the deposition of coke, but the amount of coke percipitated was not increased with the lapse of the flow time, thus manifesting that remarkable deterioration of the activity could not be recognized.

Example 3

A β-zeolite (Ce-βZ of H type) (Sample 2) was prepared in the same manner as described in Example 1 except that the amount of $Ce(NO_3)_3$ used was 0.026 mmol.

A chemical composition (molar ratio) of this zeolite was as follows:

$SiO_2$: 1, $Al_2O_3$: 001, $CeO_2$: 0.0064.

Using the above catalyst, an isomerizing reaction of n-hexane was checked under the same reaction conditions.

Table 2 shows the flow time (passing time) in case of using Sample 2, a conversion rate of n-hexane, a yield and selection rate of isoparaffin, and an amount of coke precipitated (% by weight). It is understood that even if the flowing time has elapsed, the amount of coke precipitated was not increased and no remarkable deterioration was recognized in the catalytic activity.

TABLE 2

| Flowing time (min) | Conversion rate of n-hexane (%) | Isoparaffin Yield (%) | Selection rate (%) | Amount of coke formed (%) |
|---|---|---|---|---|
| 10 | 32.48 | 15.36 | 47.3 | — |
| 60 | 31.31 | 14.34 | 45.89 | — |
| 110 | 30.17 | 13.63 | 45.18 | — |
| 160 | 31.76 | 14.08 | 44.33 | — |
| 210 | 28.53 | 12.66 | 44.37 | — |
| 260 | 24.83 | 10.79 | 43.47 | 0.54 |

Comparative Example 1

A β-zeolite (βZ of type H, Comparative Sample 1) was prepared according to the chemical composition of Example 1 except that cerium was not contained.

A chemical composition (molar ratio) of this zeolite was as shown below:

$SiO_2$: 1, $Al_2O_3$: 0.01

Excluding cerium, the chemical composition was identical with that of Sample 1.

Using the Comparative Sample 1 as catalyst, an isomerizing reaction was carried out under the same reaction conditions as those shown in Example 3.

Table 3 shows the flow time (passing time) in case of using Comparative Sample 1, a conversion rate of n-hexane, a yield and selection rate of isoparaffin, and an amount of coke precipitated (% by weight). It is noted that a β-zeolite free of cerium is lower in initial activity and the amount of

TABLE 1

| Flowing time (min) | Conversion rate of n-hexane (%) | Isoparaffin Yield (%) | Selection rate (%) | Amount of coke formed (%) |
|---|---|---|---|---|
| 10 | 42.98 | 23.14 | 53.85 | 0.96 |
| 60 | 39.94 | 19.54 | 48.93 | 0.95 |
| 110 | 33.47 | 16.07 | 48.00 | 1.05 |
| 160 | 31.68 | 14.54 | 45.91 | 1.15 |
| 210 | 38.5 | 18.39 | 47.77 | 1.20 |
| 260 | 28.91 | 13.02 | 45.02 | 1.42 | coke precipitated becomes larger with the lapse of time, thus showing a remarkable depression in the conversion rate.

TABLE 3

| Flowing time (min) | Conversion rate of n-hexane (%) | Isoparaffin Yield (%) | Isoparaffin Selection rate (%) | Amount of coke formed (%) |
|---|---|---|---|---|
| 60 | 25 | 15.47 | 61.87 | 2.43 |
| 110 | 11.22 | 6.17 | 54.97 | 2.35 |
| 160 | 10.96 | 6.09 | 55.6 | 3.62 |
| 210 | 11.47 | 6.23 | 54.29 | 3.7 |
| 260 | 9.99 | 4.80 | 48.03 | 3.85 |

Comparative Example 2

In order to investigate the effect of cerium in the dry gel process, Comparative Sample 1 was impregnated with cerric nitrate to prepare a βZ containing cerium carried thereon (Comparative Sample 2).

A chemical composition (molar ratio) of this zeolite was as shown below:

$SiO_2$: 1, $Al_2O_3$: 0.01, $CeO_2$: 0.03.

Using the Comparative Sample 2 as catalyst, an isomerizing reaction was carried out under the same reaction conditions as those shown in Example 2.

Table 4 shows the flow time (passing time) in case of using Comparative Sample 2, a conversion rate of n-hexane, a yield and selection rate of isoparaffin, and an amount of coke precipitated (% by weight). In case of the Comparative Sample 2, the initial catalytic activity was low and the conversion rate became lower with the lapse of the flowing time, thus decreasing the yield of isoparaffin. Despite lower conversion rate, the amount of coke formed was increased.

TABLE 4

| Flowing time (min) | Conversion rate of n-hexane (%) | Isoparaffin Yield (%) | Isoparaffin Selection rate (%) | Amount of coke formed (%) |
|---|---|---|---|---|
| 60 | 20.76 | 11.80 | 56.84 | 1.83 |
| 110 | 16.86 | 9.53 | 56.53 | 189 |
| 160 | 14.9 | 8.55 | 57.37 | 2.15 |
| 210 | 13.36 | 6.81 | 50.99 | 2.22 |
| 260 | 12.45 | 6.43 | 51.62 | 2.41 |

Comparative Example 3

(Synthesis of Ce-βZ According to the Hydrothermal Process)

A 35 wt. % aqueous solution containing 75 mmol of tetraethylammonium hydroxide (TEAOH) was mixed with a 25.2 wt. % of aqueous solution of 45 mmol of NaOH. To this mixture was added 7.51 g of a colloidal silica (Ludox HS-40) containing 150 mmol of $SiO_2$ and the whole was stirred for 30 minutes.

A solution of 1.5 mmol of $Al_2(SO_4)_3$ in 30.63 ml of warmed distilled water was then added to this mixture, and the whole was agitated for 30 minutes. To the mixture was added 1.99 mmol of $Ce(NO_3)_3$ and the whole was then sired for 2 hours. A gel thus obtained was placed in an autoclave (125 ml) the inside of which was lined with Teflon®. The autoclave was heated for 7 days at 150° C. whereby the dried gel was crystallized. The autoclave was then cooled with cold water and the resultant zeolite was washed with water and dried at room temperature.

The zeolite was then baked at 550° C. to burn the organic template (TEAOH) contained therein. An aqueous solution of ammonium nitrate was acted on the based product to convert it into the ammonium salt, and then baked for 7 hours at 550° C. whereby a β-zeolite containing cerium (Comparative Sample 3) of proton type (Model H) was obtained.

A chemical composition (molar ratio) of this zeolite was as shown below:

$SiO_2$: 1, $Al_2O_3$: 003, $CeO_2$: 0.007.

An X-ray diffraction pattern of this zeolite is shown in detail in FIG. 2

Comparative Example 4

An isomerizing reaction was carried out in the same manner as described in Example 2 except that the Comparative Sample 3 prepared in Comparative Example 3 was used as catalyst in place of the Sample 1.

Table 5 shows the flow time (passing time) in case of using Comparative Sample 3, a conversion rate of n-hexane, a yield and selection rate of isoparaffin, and an amount of coke precipitated (% by weight). It is noted that the catalytic activity was deteriorated with the lapse of the flowing time while the formation of a considerable amount of coke was detected.

TABLE 5

| Flowing time (min) | Conversion rate of n-hexane (%) | Isoparaffin Yield (%) | Isoparaffin Selection rate (%) | Amount of coke formed (%) |
|---|---|---|---|---|
| 10 | 53.83 | 30.28 | 56.26 | — |
| 60 | 34.45 | 17.72 | 51.43 | — |
| 110 | 25.16 | 12.43 | 49.4 | — |
| 160 | 29.2 | 14.81 | 50.71 | — |
| 210 | 22.32 | 10.88 | 48.73 | — |
| 260 | 18.88 | 8.74 | 46.27 | 8.15 |

Comparative Example 5

In the same manner as in Example 2, Na type βZ was subjected to ion-exchange thereby preparing a Ce-βZ into which cerium had been introduced (Comparative Sample 4).

A chemical composition (molar ratio) of this zeolite was as shown below:

$SiO_2$: 1, $Al_2O_3$: 0.01, $CeO_2$: 0.0062.

Using the Comparative Sample 4 prepared in Comparative Example 5 as catalyst, an isomerizing reaction of n-hexane was carried out according to the same process as described in Example 2.

Table 6 shows the flow time (passing time) in case of using Comparative Sample 4, a conversion rate of n-hexane, a yield and selection rate of isoparaffin, and an amount of coke precipitated (% by weight). It is noted that the initial catalytic activity was low and the catalytic activity was seriously deteriorated with the lapse of the flowing time while the formation of a considerable amount of coke was detected.

TABLE 6

| Flowing time (min) | Conversion rate of n-hexane (%) | Isoparaffin | | Amount of coke formed (%) |
| --- | --- | --- | --- | --- |
| | | Yield (%) | Selection rate (%) | |
| 60 | 30.77 | 15.37 | 49.73 | — |
| 110 | 23.72 | 11.46 | 48.31 | — |
| 160 | 19.7 | 9.41 | 47.78 | — |
| 210 | 19.33 | 9.19 | 47.52 | — |
| 260 | 20.71 | 9.82 | 47.44 | 4.77 |

EFFECT OF THE INVENTION

As is evident from the foregoing description, the specific β-zeolite containing cerium as prepared according to the dry gel process exhibits a high degree of isomerization effect for n-paraffin without causing any environmental pollution and the catalytic activity is prolonged without deterioration for a long period of time. In addition, such specific β-zeolite scarcely produces carbonaceous materials in the course of the isomerization which are heretofore known to shorten the catalyst life. Thus, the present invention brings about a significant improvement in the field of producing mineral fuels.

It is understood that the preceding representative examples may be varied within the scope of the present specification both as to reactants and reaction conditions, by those skilled in the art to achieve essentially the same results.

As many widely different embodiments of the present invention may be made without departing from the spirit and scope thereof, it is to be construed that the present invention is not limited to the specific embodiments thereof except as defined in the appended claims.

What is claimed is:

1. A catalyst composition for the isomerization of n-paraffin comprising a β-zeolite and cerium, wherein said catalyst composition is synthesized according to a dry gel process and has an average particle diameter of 0.01 to 0.1 μm and wherein the cerium is present in an amount providing an atomic ratio Ce/Si of the cerium atoms to the silicon atoms in the β-zeolite of 0.001 to 0.2.

2. A process for isomerizing n-paraffin comprising bringing n-paraffin into contact with the catalyst composition as set forth in claim 1.

3. A process for isomerizing n-paraffin as set forth in claim 2, wherein said catalyst composition is pressure-molded into a shaped body.

4. A process for isomerizing n-paraffin as set forth in claim 3, wherein said catalyst composition is pressure-molded together with a binder.

* * * * *